US008302458B2

(12) United States Patent
Ali Hassan et al.

(10) Patent No.: US 8,302,458 B2
(45) Date of Patent: Nov. 6, 2012

(54) PORTABLE ANALYTICAL SYSTEM FOR DETECTING ORGANIC CHEMICALS IN WATER

(75) Inventors: Kazi Zulfiqur Ali Hassan, Huntsville, AL (US); William M. Cost, Hartselle, AL (US); Curtis D. Mowry, Albuquerque, NM (US); Michael P. Siegal, Albuquerque, NM (US); Alex Robinson, Albuquerque, NM (US); Joshua J. Whiting, Los Lunas, NM (US); Stephen W. Howell, Albuquerque, NM (US)

(73) Assignee: Parker-Hannifin Corporation, Cleveland, OH (US)

( * ) Notice: Subject to any disclaimer, the term of this patent is extended or adjusted under 35 U.S.C. 154(b) by 437 days.

(21) Appl. No.: 12/106,734

(22) Filed: Apr. 21, 2008

(65) Prior Publication Data

US 2008/0289397 A1    Nov. 27, 2008

Related U.S. Application Data

(60) Provisional application No. 60/913,051, filed on Apr. 20, 2007, provisional application No. 61/031,396, filed on Feb. 26, 2008.

(51) Int. Cl.
G01N 30/02 (2006.01)
G01N 30/76 (2006.01)
G01N 29/02 (2006.01)
(52) U.S. Cl. .......................... 73/23.4; 73/24.01; 73/24.06
(58) Field of Classification Search .................... 73/23.4, 73/24.01, 24.06
See application file for complete search history.

(56) References Cited

U.S. PATENT DOCUMENTS

| 4,230,464 | A | * | 10/1980 | Bonmati et al. ................. 95/22 |
| 5,151,110 | A | | 9/1992 | Bein et al. |
| 5,258,171 | A | * | 11/1993 | Eltomi .......................... 423/477 |
| 5,426,300 | A | | 6/1995 | Voss et al. |
| 5,492,838 | A | * | 2/1996 | Pawliszyn .................... 436/178 |
| 5,917,135 | A | | 6/1999 | Michaels et al. |
| 5,920,143 | A | | 7/1999 | Tarui et al. |
| 6,074,461 | A | * | 6/2000 | Wilson .......................... 96/102 |
| 6,085,576 | A | | 7/2000 | Sunshine et al. |
| 6,134,944 | A | | 10/2000 | Yu et al. |
| 6,234,006 | B1 | | 5/2001 | Sunshine et al. |
| 6,244,096 | B1 | | 6/2001 | Lewis et al. |
| 6,295,861 | B1 | | 10/2001 | Tom et al. |

(Continued)

FOREIGN PATENT DOCUMENTS

JP    2234507    9/1990

(Continued)

OTHER PUBLICATIONS

Lu, Chia-Jung et al. "A Dual-Adsorbent Preconcentrator for a Portable Indoor-VOC Microsensor System", Anal. Chem., vol. 73, No. 14, Jul. 15, 2001, pp. 3449-3457.*

(Continued)

*Primary Examiner* — Daniel Larkin
(74) *Attorney, Agent, or Firm* — Renner, Otto, Boisselle & Sklar, LLP

(57) ABSTRACT

A portable analytical system for detecting organic chemicals in water comprising a miniature preconcentrator and a SAW detector, the latter being characterized by a nanoporous carbon coating that provides improved response compared to prior art polymer coatings, particularly when detecting low concentrations of trihalomethane chemicals, such as chloroform and bromoform.

19 Claims, 11 Drawing Sheets

U.S. PATENT DOCUMENTS

| | | | |
|---|---|---|---|
| 6,319,724 B1 | 11/2001 | Lewis et al. |
| 6,387,329 B1 | 5/2002 | Lewis et al. |
| 6,418,783 B2 | 7/2002 | Sunshine et al. |
| 6,422,061 B1 | 7/2002 | Sunshine et al. |
| 6,455,319 B1 | 9/2002 | Lewis et al. |
| 6,467,333 B2 | 10/2002 | Lewis et al. |
| 6,566,983 B2 | 5/2003 | Shin |
| 6,610,367 B2 | 8/2003 | Lewis et al. |
| 6,631,333 B1 | 10/2003 | Lewis et al. |
| 6,658,915 B2 | 12/2003 | Sunshine et al. |
| 6,684,683 B2 | 2/2004 | Potyrailo et al. |
| 6,691,702 B2 | 2/2004 | Appel et al. |
| 6,703,241 B1 | 3/2004 | Sunshine et al. |
| 6,759,010 B2 | 7/2004 | Lewis et al. |
| 6,772,513 B1 * | 8/2004 | Frye-Mason et al. ............ 29/840 |
| 6,837,095 B2 | 1/2005 | Nakayama et al. |
| 6,841,391 B2 | 1/2005 | Lewis et al. |
| 6,870,234 B2 | 3/2005 | Brewer et al. |
| 6,883,364 B2 | 4/2005 | Sunshine et al. |
| 6,890,715 B1 | 5/2005 | Lewis et al. |
| 6,914,220 B2 | 7/2005 | Tian et al. |
| 6,914,279 B2 | 7/2005 | Lu et al. |
| 6,962,675 B2 | 11/2005 | Lewis et al. |
| 6,981,947 B2 | 1/2006 | Melker |
| 7,047,792 B1 | 5/2006 | Bhethanabotla et al. |
| 7,052,468 B2 | 5/2006 | Melker et al. |
| 7,052,854 B2 | 5/2006 | Melker et al. |
| 7,066,985 B2 | 6/2006 | Deane et al. |
| 7,078,237 B1 * | 7/2006 | Mowry et al. .................. 436/147 |
| 7,089,780 B2 | 8/2006 | Sunshine et al. |
| 7,104,963 B2 | 9/2006 | Melker et al. |
| 7,122,152 B2 | 10/2006 | Lewis et al. |
| 7,135,059 B2 | 11/2006 | Deane et al. |
| 7,141,446 B2 | 11/2006 | Brewer et al. |
| 7,144,553 B2 | 12/2006 | Lewis et al. |
| 7,147,695 B2 | 12/2006 | Mitra |
| 7,153,272 B2 | 12/2006 | Talton |
| 7,168,298 B1 | 1/2007 | Manginell et al. |
| 7,189,353 B2 | 3/2007 | Lewis et al. |
| 7,194,891 B2 | 3/2007 | Tuller et al. |
| 7,282,676 B1 | 10/2007 | Bouchier et al. |
| 7,299,711 B1 | 11/2007 | Linker et al. |
| 7,399,449 B1 * | 7/2008 | Oborny et al. ................. 422/102 |
| 7,430,928 B2 * | 10/2008 | Grate et al. ................. 73/863.21 |
| 2002/0073764 A1 | 6/2002 | Guerra et al. |
| 2005/0226773 A1 | 10/2005 | Liu |
| 2005/0289351 A1 | 12/2005 | England et al. |
| 2006/0088445 A1 | 4/2006 | Lewis et al. |
| 2006/0130611 A1 * | 6/2006 | Lynn ............................... 75/367 |
| 2006/0210425 A1 | 9/2006 | Mirkarimi |
| 2007/0062255 A1 | 3/2007 | Talton |
| 2007/0085446 A1 | 4/2007 | Chen |

FOREIGN PATENT DOCUMENTS

| | | |
|---|---|---|
| WO | 9631773 | 10/1996 |
| WO | 2005066288 | 7/2005 |

OTHER PUBLICATIONS

Siegal, M.P. et al., "Nannporous Carbon Films for Gas Microsensors", Langmuir, vol. 20, 2004, pp. 1194-1198.*

Groves, W.A. et al., "Analyzing Organic Vapors in Exhaled Breath Using a Surface Acoustic Wave Sensor Array with Preconcentration: Selection and Characterization of the Preconcentrator Adsorbent", Analytica Chimica Acta, vol. 371, 1998, pp. 131-143.*

Matney, M.L. et al., "Multisorbent Tubes for Collecting Volatile Organic Compounds in Spacecraft Air", AIHAJ, vol. 61, Jan./Feb. 2000, pp. 69-75.*

M.P. Siegal et al., "Nanoporous-Carbon Adsorbers for Chemical Microsensors," Sandia Report, SAND2004-5277, Nov. 2004, 35 pages.

M.P. Siegal and W.G. Yelton, "Nanoporous-Carbon Coatings for Gas-Phase Chemical Microsensors," Advances in Science and Technology, vol. 48, 2006, pp. 161-168.

M.P. Siegal et al., "Nanoporous-carbon films for microsensor preconcentrators," Appl. Phys. Lett., vol. 80, No. 21, May 27, 2002, pp. 3940-3942.

Curtis D. Mowry et al., "Real-time Discriminatory Sensors for Water Contamination Events: LDRD 52595 Final Report," Oct. 2005, 57 pages.

Curtis D. Mowry et al., "Recent Advancements Toward Field Portable Detection of THMs by Surface Acoustic wave Detection," Mar. 2007, 27 pages.

Curtis D. Mowry et al., "Portable Field System for Rapid, On-Site Detection of Disinfection Byproducts in Water," Nov. 2005, 26 pages.

Tenax TA Adsorbent Resin Physical Properties, accessed Apr. 8, 2008, http://www.sisweb.com/index/referenc/tenaxtam.htm, 3 pages.

Inficon Hapsite Situprobe, 2007, 2 pages.

C. Eric Boswell, "Fast and Efficient Volatiles Analysis by Purge and Trap GC/MS," 1999, 5 pages.

Surface acoustic wave, accessed Apr. 8, 2008, http://en.wikipedia.org/wiki/Surface_acoustic_wave, 2 pages.

Acoustic Wave Technology Sensors, Drafts, Oct. 2000 http://www.sensorsmag.com/articles/1000/68/main.shtml, 13 pages.

* cited by examiner

PORTABLE ANALYTICAL SYSTEM FOR DETECTING ORGANIC CHEMICALS IN WATER

RELATED APPLICATIONS

This application claims the benefit of U.S. Provisional Application Nos. 60/913,051 filed Apr. 20, 2007 and 61/031,396 filed Feb. 26, 2008. This application also is related to U.S. patent application Ser. No. 11/934,996 filed Nov. 5, 2007, and entitled "Portable Analytical System for Detecting Organic Chemicals in Water", in that the present invention relates in particular to improvements applicable to the system disclosed in the '966 application. All of the aforesaid applications are hereby incorporated herein by reference in their entireties.

FIELD OF THE INVENTION

The present invention relates to chemical analysis systems and methods and in particular to a portable analytical system for detecting organic chemicals in water.

BACKGROUND

Purge and trap is a well known technique for the extraction (purging or sparging) of chemicals out of liquids (including water). In a typical laboratory method, an inert gas, often helium, is used to transfer chemicals from the liquid phase to the gas phase. Once in the gas phase the chemicals are transferred to a variety of traps such as an adsorbent bed or liquid nitrogen cold trap.

Several commercial portable systems provide for detection of water-borne volatiles. One such system, the Inficon Scentograph CMS 200 gas chromatograph, is a portable field gas chromatograph that can be powered in a DC mode by rechargeable batteries. For fixed-location operations, the unit can be connected to an AC source. The unit includes an internal supply cylinder for a carrier gas, in particular argon for a MAID/ECD configuration or helium for a photoionization detector (PID) or thermal conductivity detector (TCD) configuration. The instrument further comprises a GC module and a detector module. The GC module includes an oven with two stage temperature ramping capability, columns, and detector(s). Several different detectors are available for different applications. An argon ionization detector (AID) provides detection of organic compounds having an ionization potential of 11.7 eV or below, including halomethanes and haloethanes. This detector purportedly is capable of detecting these compounds, as well as other hydrocarbons, down to low ppb levels. A micro argon ionization detector (MAID) is a small volume, higher sensitivity version of the AID, that is used with capillary columns with detection limits purportedly at the sub ppb levels. An electron capture detector (ECD) is a selective detector used for the detection of halogenated hydrocarbons, PCB's, pesticides, and nitro-based compounds. A thermal conductivity detector (TCD) is used primarily for the detection of natural gases in concentrations ranging from 100 ppm to percent levels. A photoionization detector (PID) uses an ultraviolet lamp to ionize and detect hydrocarbons having ionization potentials of 10.6 eV or less.

A drawback of the Inficon Scentograph CMS 200 gas chromatograph and similar instruments is high cost and the requirement for an on-board carrier gas.

Also known is the DR 2800 Portable Spectrophotometer manufactured by Hach Company that uses a colorimetric system that can detect THM chemicals. This system does not speciate THM species but instead provides one concentration value for over four chemicals. The system uses multiple chemical packets that an analyst has to open and add to the water sample.

Still another instrument is the ZNOSE® analyzer available from Electronic Sensor Technology. The ZNOSE® Model 4200 is a portable real time analyzer that can detect and analyze vapors and identify traces of organic, biological and chemical compounds. As understood, the analyzer is a surface acoustic wave (SAW) detector-based system. For volatiles in water, the analyzer performs a headspace analysis. An optional desorption tube collection device is not portable and requires AC power. An optional water sample heater is also not portable and requires AC power.

Related U.S. patent application Ser. No. 11/934,996

The '966 patent application discloses a self-contained instrument that does not require secondary gases (for purging or analysis), that speciates (separates) the chemicals, e.g. THMs, for individual quantitation, and uses an acoustic wave detector. This portable field system purges vapors, using air (not helium, although helium or other carrier gases can be used), from a water sample, collects them on an adsorbent bed that is subsequently heated to send the chemical species down a separation column to the detector. The detector in this system is a four channel surface acoustic wave (SAW) detector developed by Sandia Corporation. The system controls the timing of valves, signal processing, heating cycles, data collection from the SAW detector, and output of ASCII text for plotting and analysis.

SUMMARY OF THE INVENTION

The present invention provides improvements in chemical analysis systems and methods and in particular improvements in a portable analytical system for detecting organic chemicals in water. An improved preconcentrator (collector) is used to collect volatile chemicals out of a water sample and an improved surface acoustic wave (SAW) detector is also provided. These improvements may be employed individually or collectively in a system that purges the chemicals (e.g. four trihalomethane chemicals of interest) from a sample (e.g. water sample by bubbling air through the sample), collects (e.g. traps) the purged chemicals in a preconcentrator, separates the chemical temporally as through use of a CG column, and detects the chemicals.

The improved preconcentrator improves upon previously used preconcentrators by eliminating the need for fused silica capillary interface junctions. This makes the preconcentrator more rugged and easier to manufacture.

The improved SAW detector is characterized by a nanoporous carbon coating that provides improved response compared to prior art polymer coatings, particularly when detecting low concentrations of trihalomethane chemicals, such as chloroform and bromoform. The detector may be provided as a lower cost one channel SAW device used to achieve improved performance (lower detection levels).

In a preferred implementation, a portable field instrument according to the invention is based on a typical purge and trap system where chemicals (e.g. purgeable trihalomethane compounds) in water are purged by a carrier gas (e.g. air, helium or nitrogen) and collected in an adsorbent bed (e.g. preconcentrator). The preconcentrator is then heated to desorb the trihalomethane compounds and pass them through a separator (e.g. a gas chromatograph column). The sample from the gas chromatograph column is carried to the carbon-coated SAW detector. The SAW detector changes its frequency depending on the mass of compound adsorbed and desorbed on the SAW detector. The compounds are identified by the retention time in the gas chromatograph column. The mass quantity of the compounds is measured by the change of frequency of the SAW device.

Accordingly, a system and method for detecting organic compounds in water comprises a preconcentrator for collecting the compounds; a gas chromatograph column for separating the compounds as desorbed from the preconcentrator; and a surface acoustic wave detector for determining the mass of the compounds separated by the gas chromatograph.

The system and method are further characterized by any one or more of the following features:
- the surface acoustic wave detector changes its frequency depending on the mass of compound adsorbed and desorbed on a sensing surface.
- the sensing surface has a porous carbon coating.
- the porous carbon coating is a nanoporous carbon coating.
- the nanoporous carbon coating was applied by pulsed laser deposition.
- the carbon is deposited between input and output transducers of the detector near the 248 nm (UV laser light) ablation limit ~1.3 J/cm$^2$, and attenuation of the ablated species is carried out by an inert background gas.
- the operating frequency of the surface acoustic wave detector is greater than 10 MHz and less than 200 MHz.
- the operating frequency of the surface acoustic wave detector is greater than 50 MHz and less than 150 MHz.
- the operating frequency of the surface acoustic wave detector is about 100 MHz.
- a data acquisition device for receiving and processing a frequency output of the surface acoustic wave detector.
- the preconcentrator includes a porous polymer resin material as an adsorber.
- a sample purger for purging chemicals from a sample for adsorption in the preconcentrator.

According to another aspect of the invention, there is provided a portable field instrument for detecting purgeable trihalomethane compounds in water, comprising a sample vessel wherein chemicals are purged and entrained in a carrier gas; a preconcentrator connected to the sample purger for adsorbing the chemicals from the carrier gas; a heater for heating the preconcentrator for desorbing the trihalomethane compounds; a gas chromatograph column to which the desorbed compounds are passed from the preconcentrator; a heater for heating the gas chromatograph column for causing the compounds to desorb after different retention times in the gas chromatograph column; and a surface acoustic wave detector to which the compounds are sequentially passed from the gas chromatograph column, the frequency of the surface acoustic wave detector changing as a function of the mass of compound adsorbed and desorbed from a sensing surface of the surface acoustic wave detector, whereby the mass quantity of the compounds is measured by the change of frequency of the surface acoustic wave device.

Further features of the invention will become apparent from the following detailed description when considered in conjunction with the drawings.

DETAILED DESCRIPTION

Figure 1:
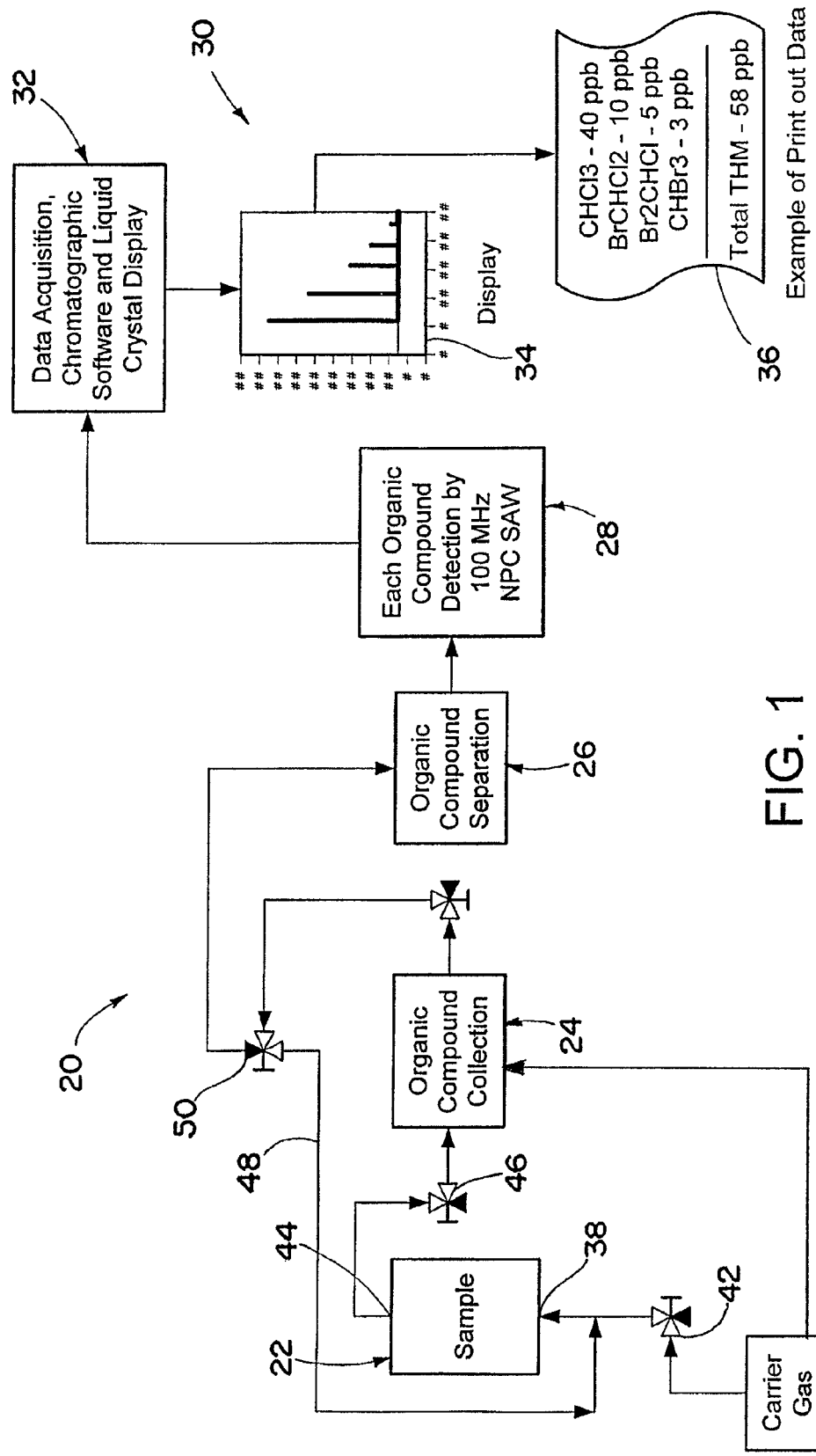
FIG. 1 is a diagrammatic illustration of an exemplary chemical analysis system according to the invention, depicting a purging cycle of operation.

Referring now to the drawings in detail and initially to FIG. 1, an exemplary chemical analysis system according to the invention is indicated generally by reference numeral 20. The system 20 generally comprises a sample vessel 22, a collector 24, a separator 26, a detector 28, and a data acquisition system 30. The data acquisition system includes a processor 32, a display 34 and other output device(s) 36 such as communications port, printer, etc. The system 20 may further comprise a controller for controlling the timing of valves, signal processing, heating cycles, data collection from the detector, and output of the data acquisition system for plotting, analysis, etc. In the illustrated system, the functions of the controller are carried out by the data acquisition system 30.

The illustrated system has particular application as a system for detecting trihalomethane compounds in water and will be chiefly described in this context. It should be understood, however, that this is exemplary and a system according to the invention may have other applications as well, such as other organic compounds typically with molecular weights lower than 4000 Daltons.

The sample vessel 22 may be of any suitable type, such as a graduated vessel for holding a prescribed amount of a sample liquid, such as water, from which the chemicals of interest are to be purged. The vessel has an inlet 38, typically at the bottom thereof, through which a carrier gas, from a supply 40, is introduced into the vessel for passage through the sample liquid. In a portable embodiment for detecting organic compounds in water, the carrier gas may be air and the supply need be nothing more than a pump connected to the sample vessel via a control valve 42 for pumping or pulling air through the sample vessel. The sample vessel further has an outlet 44 through which the gas with entrained chemical(s) exits the vessel for passage to an inlet of collector 24 via a control valve 46. During the purging cycle, carrier gas exiting the collector is circulated back through the sample vessel 22 by a recirculation loop 48 including a control valve 50.

The collector 24 preferably is a miniature chemical preconcentrator in which the chemicals are adsorbed while the carrier gas is circulated through the sample vessel and collector for a prescribed amount of time. A preferred preconcentrator is one that is designed to have 1) high efficiency chemical scrubbing (no break through), 2) sufficient chemical capacity for downstream analytical analysis, 3) minimal size, 4) minimal thermal mass for low power thermal desorption of the entrapped chemicals, and/or 5) a built-in heater. This fills a gap between low capacity microfabricated chemical preconcentrators and large, high capacity commercial traps.

Figure 3:
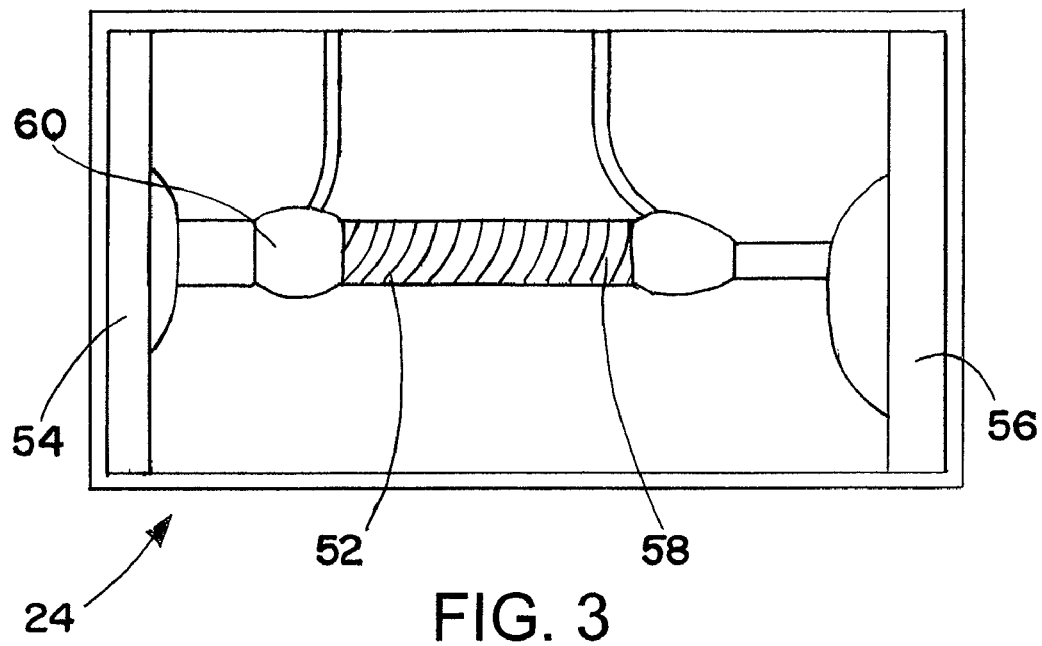
FIG. 3 is a depiction of an exemplary preconcentrator used in the system.

The collector (preconcentrator) 24 may be, for example, one or more metal collection tubes 52 of small diameter (<0.20 inch OD) disposed between upstream and downstream manifold blocks 54 and 56 as seen in FIG. 3. The tube may have a length of about 2 inches and an outer diameter of about 0.042 inch. The metal tube may be coated on its inner and outer diameter surfaces with a passivating material such as trimethyl siloxane. The interior of the tube may be filled with a suitable adsorbing material such as fine mesh, commercial chemical adsorbent beads. In a particularly advantageous system, a dual bed configuration (e.g. approximately 1 inch in length) may be used with Tenax™ porous polymer resin material being followed by a more aggressive Carboxen™ carbon-based adsorbent resin available from Supelco, Inc., coupled with reverse flow during the desorption phase). This is particularly preferred for adsorbing purged trihalomethane compounds. Such material has been found to increase efficiency, from previously used polymer coatings such as poly phenylated pheylene (PPP), modified fluorinated polyol (DKAP), polyepichlorohydrin, preconcentrator, on the order of 80% for chloroform, 100% for dichlorobromomethane (DCBM), 100% for dibromochloromethane (DBCM), and 100% for bromoform, each at 1 ppb level concentration. The collection tube 52 may be wrapped with a resistance heater 58 such as a nichrome heating wire, and a thermocouple 60 may be provided for temperature measurement. The thermocouple may be embedded in a thermally conductive epoxy. The resulting device is compact, rugged, simple to fabricate, and stable for intermittent operation up to, for example, 350 degrees C. (less for adsorbent beads that can not tolerate this temperature).

Figure 2:
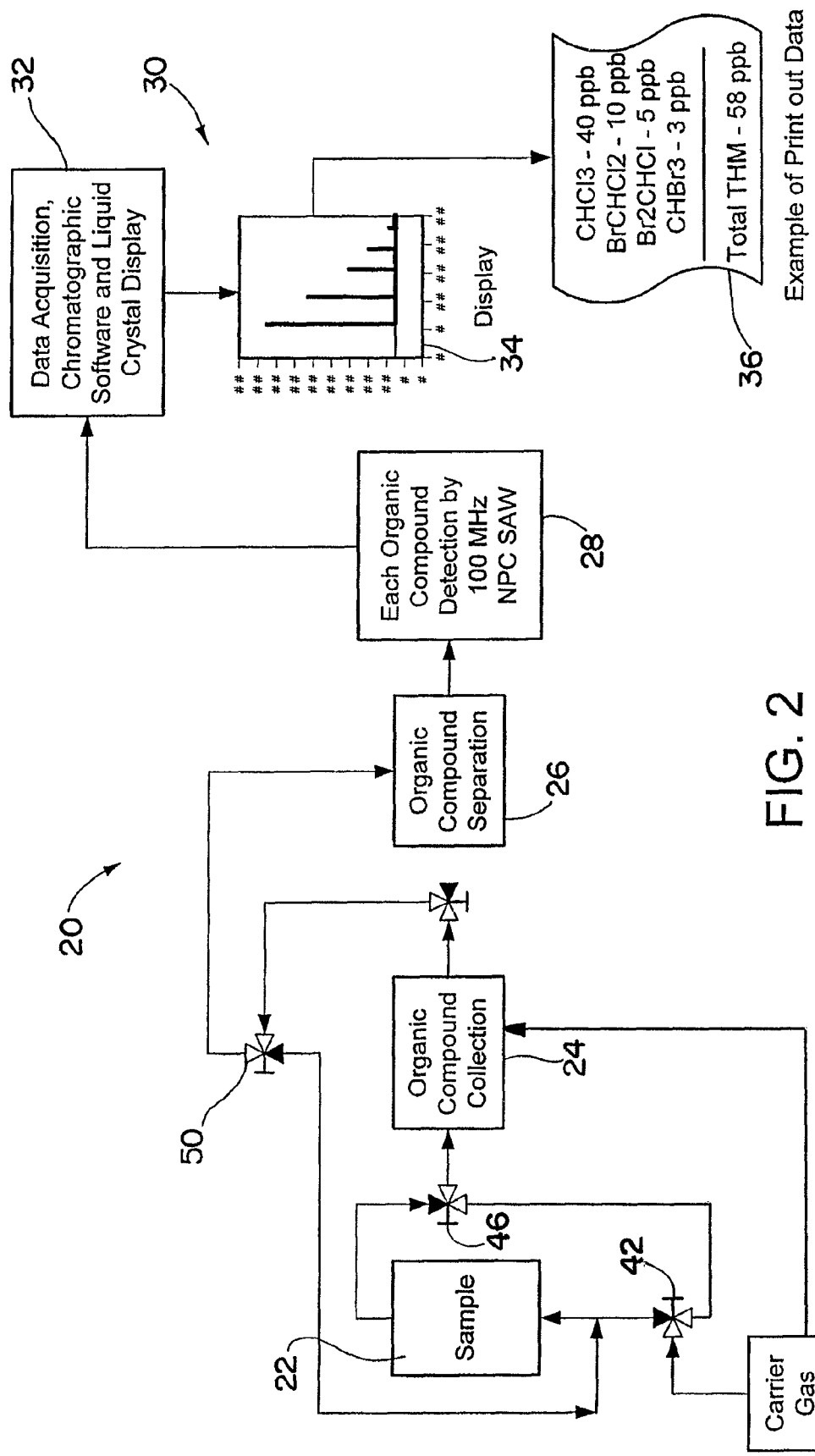
FIG. 2 is a diagrammatic illustration similar to FIG. 1, but depicting a measurement cycle of operation.

After the purging cycle is completed and as depicted in FIG. 2, the control valves 42, 46 and 50 are operated to bypass the sample vessel 22 so that the carrier gas flows directly to the collector 24 and then to the separator 26 and finally the detector 28 after which the carrier gas may be exhausted to atmosphere or to a collection device. The collector 24 is heated to desorb the purged compounds for passage through the separator 26.

Figure 4:
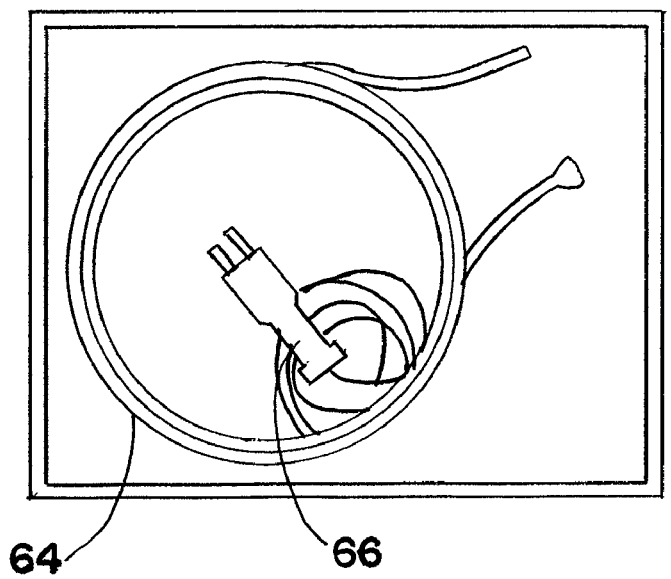
FIG. 4 is a depiction of an exemplary separator (chromatography column) used in the system.

The separator 26 preferably includes a gas chromatograph column which partially retains the chemical compounds with different affinities as they pass through the column resulting in different retention times for each compound, thereby spreading out the time each compound is delivered to the detector, so that temporal overlap does not occur or is minimized. As seen in FIG. 4, the column may be a conventional capillary tube 64 that is, for example, compactly coiled and has a length, for example, of 3 meters. The tube has associated therewith a suitable heater 66 for heating the tube to a prescribed temperature, as at a constant or controlled ramping temperature, for sequential desorption of the compounds for sequential passage to the detector 28.

The detector preferably comprises a SAW device including a piezoelectric element having a surface coated on its sensing surface with a material selected to absorb and interact with the chemical or chemicals to be detected. Interaction of the chemical with the material coating of the sensing element alters one or more properties of a surface acoustic wave, and the electrodes on the piezoelectric element detect the altered wave, producing an electrical signal.

A preferred SAW device is a 100 MHz device coated with nanoporous carbon by use of pulsed laser deposition. The nanoporous carbon coating adsorbs and desorbs the organic compounds. The frequency of the SAW device changes as a function of the change in adsorbed mass of these organic compounds. This change of frequency is converted into a voltage signal according to mass adsorption and desorption on the SAW device.

Figure 12:
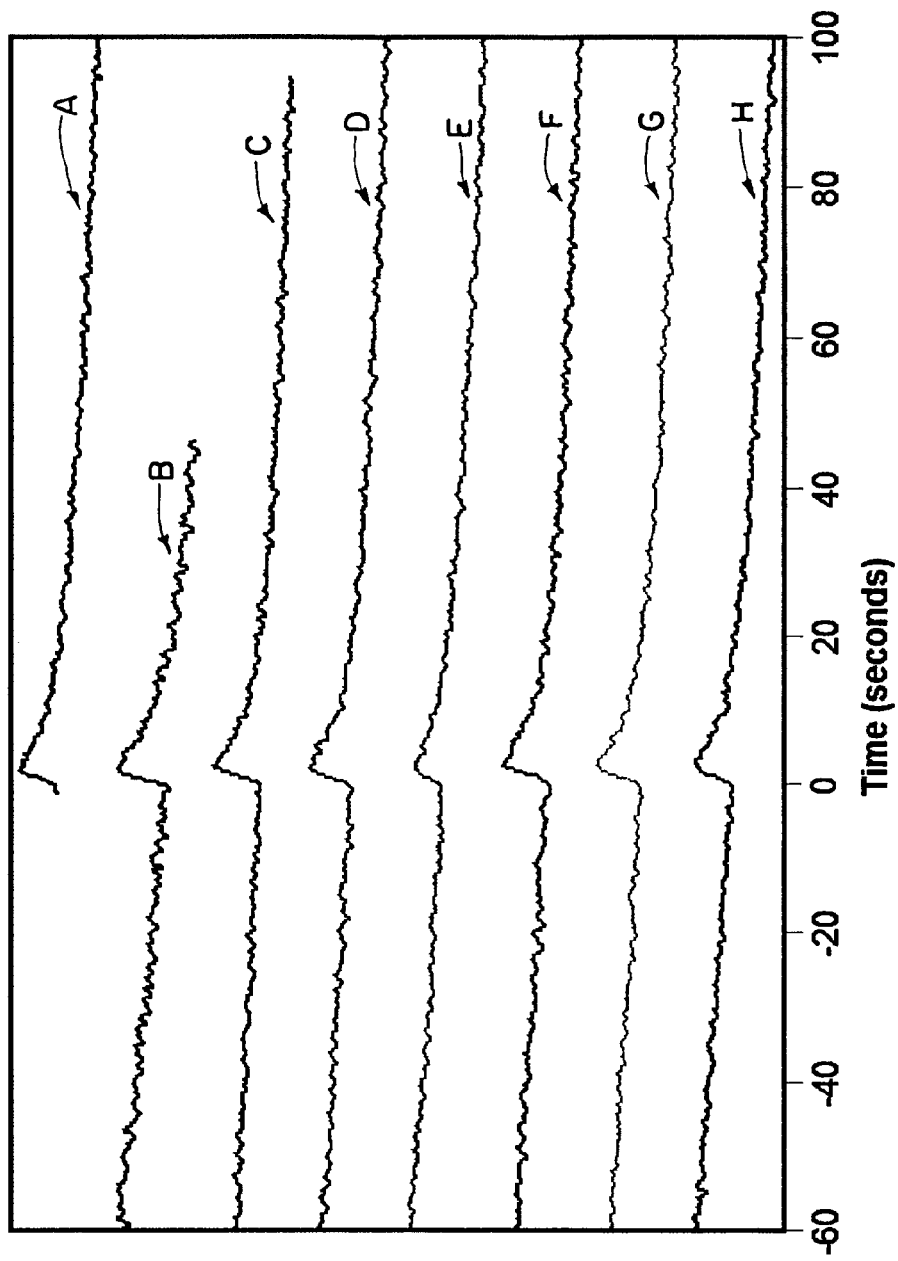
FIG. 12 is a graph showing the repeatability of chloroform detection by a 100 MHz nanoporous coated SAW detector.

The carbon may be deposited between the input and output transducers of the SAW sensor near the 248 nm (UV laser light) ablation limit ~1.3 J/cm2. In order to eliminate residual stress, the attenuation of ablated species may be carried out by an inert background gas (Ar). This combination of laser density, target-to-substrate distance and inert gas provides excellent control of carbon deposition. Detection limits can be obtained in the range of 17 ng chloroform in a 50 mL water sample, which is equivalent of 0.34 parts per billion (ppb) by weight in water samples. The repeatability of results is illustrated in FIG. 12, this demonstrating a significant improvement in the reproducibility (of response) of the nanoporous carbon coating over previous polymer coated SAWs.

Figure 5:
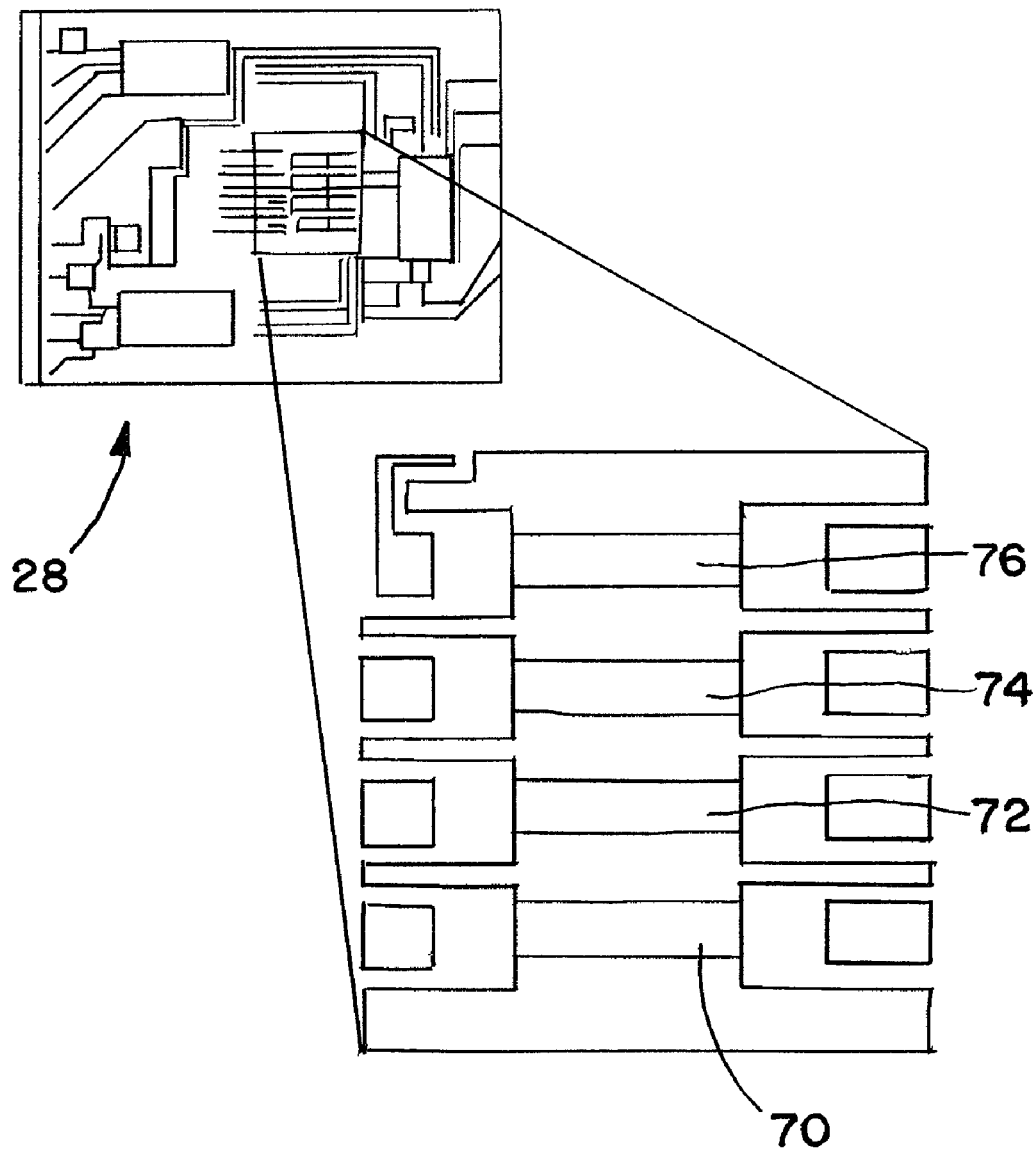
FIG. 5 is a depiction of an exemplary 500 MHz SAW detector using a polymer coating.
Figure 13:
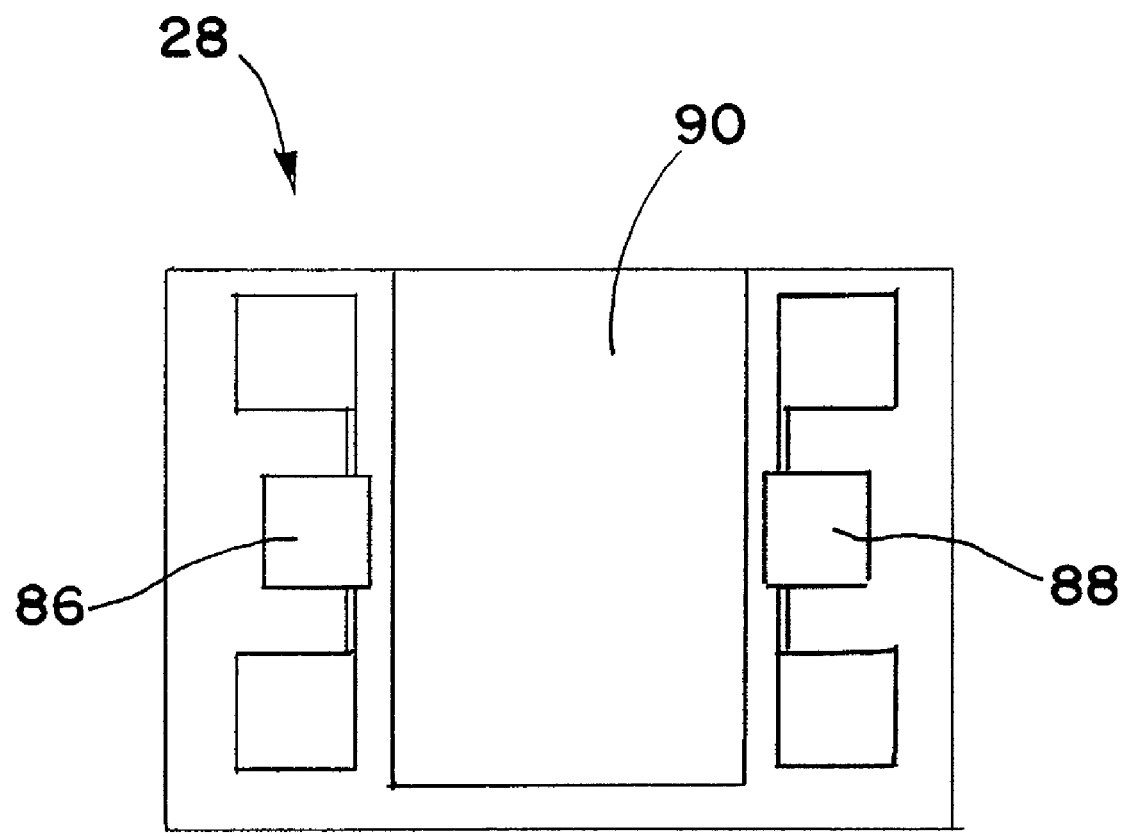
FIG. 13 is a depiction of an exemplary 100 MHz SAW detector using a nanoporous carbon coating.

An exemplary SAW detector 28 with a polymer coating is illustrated in FIG. 5. The illustrated detector includes four active sensors, three 70, 72, 74 with coating and one 76 reference. FIG. 13 is a depiction of an exemplary 100 MHz SAW detector including input and output transducers 86 and 88 and having a nanoporous carbon coating 90 applied to the sensing surface of the SAW using pulsed-laser deposition.

For further information regarding the growth of nanoporous-carbon using an energetic physical deposition process, in particular a pulsed-laser deposition, reference may be had to the following publications, which are hereby incorporated herein by reference:

M P. Siegal, D. L. Overmyer, D. R. Tallant, and P. N. Provencio, "Growth and characterization of amorphous-to-nanocrystalline carbon films", Materials Research Society Fall Meeting, Boston, Mass., December 1999.

M P. Siegal, D. L. Overmyer, W. G. Yelton, and R. J. Kottenstette, "Nanoporous carbon films for MicroChemLab™ Sensors", Materials Research Society Spring Meeting, San Francisco, Calif. Apr. 16-20, 2001.

M. P. Siegal, D. L. Overmyer, R. J. Kottenstette, D. R. Tallant, and W. G. Yelton, "Nanoporous-carbon films for microsensor preconcentrators", Appl. Phys. Lett. 80, 3940 (2002).

M. P. Siegal, W. G. Yelton, D. L. Overmyer, and P. P. Provencio, "Nanoporous-carbon films for gas microsensors", Langmuir, 20, 1194 (2004).

M. P. Siegal and W. G. Yelton, "Nanoporous-carbon coatings for gas-phase chemical microsensors", Advances in Science and Technology, 48, 161 (2006).

By way of a particular example, nanoporous carbon coating growth may be carried out using a pulse laser ablation process. This process is a combination of desired pressure and energy of pulse laser ablation of graphite material in presence of an inert gas environment as well as a suitable distance between target to substrate distance. Exemplary parameters for this process are pressure between about 120 to about 170 mTorr, pulse laser energy ablation between about 1 to about 3 J/cm$^2$, target to substrate distance between about 2 to 3 inches and Argon as the inert gas. The pulse laser deposition process can make a carbon-coated SAW, which can detect low detection levels of low molecular weight organic compounds. The carbon coating on SAW with a carbon density of about 0.8 to about 1.3 g/cm³ and a coating thickness of about 1 to about 3 µm will have, for example, the capability of detecting chloroform at 0.43 parts per billion. Accordingly, the coating thickness may be greater than about 0.5 µm and more particularly greater than about 1 µm. Additionally or alternatively, the coating thickness may be no greater than about 10 µm, or more particularly no greater than about 5 µm, and still more particularly no greater than about 3 µm. As for density, the density may be greater than about 0.5 g/cm³ and more particularly greater than about 0.8 g/cm³; and the density mat be no greater than about 2 g/cm³, more particularly no greater than about 1.5 g/cm³, and still more particularly no greater than about 1.3 g/cm³.

Figure 6:
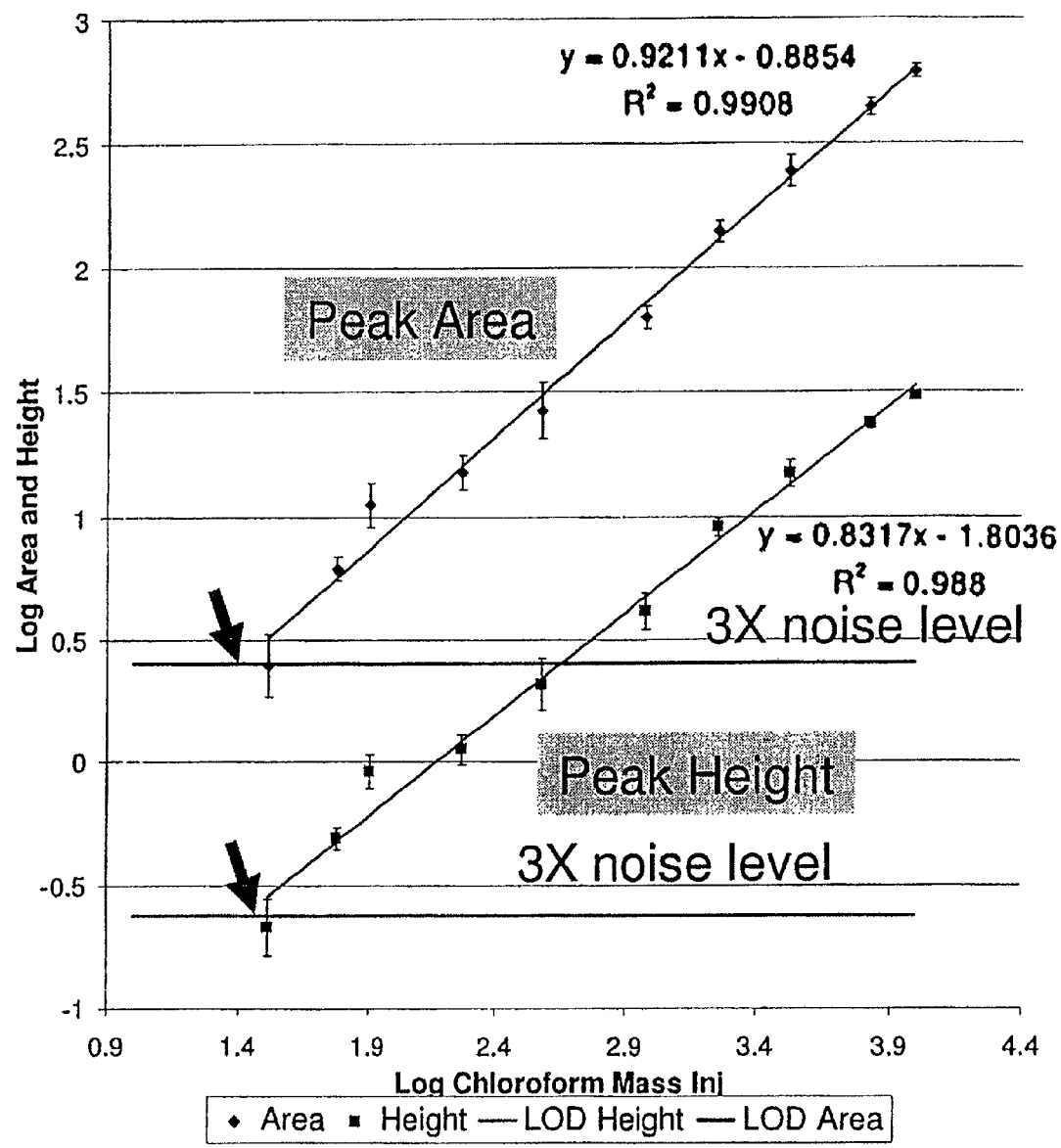
FIG. 6 is a graph showing limit of detection testing for chloroform using a 100 MHz carbon coated SAW device according to the invention.

The nanoporous carbon coating is not susceptible to degradation when subjected to chloroform and other organic volatiles, as were previously used polymer coatings. This provides a longer life and allows for reduction of sample sizes. A limit of detection data for an exemplary system using a carbon coated 100 MHz SAW device is shown in the FIG. 6. The observed limit of detection can be drawn to lower than one ppb of chloroform with the 100 MHz carbon coated SAW detector and above described preferred preconcentrator.

Figure 7:
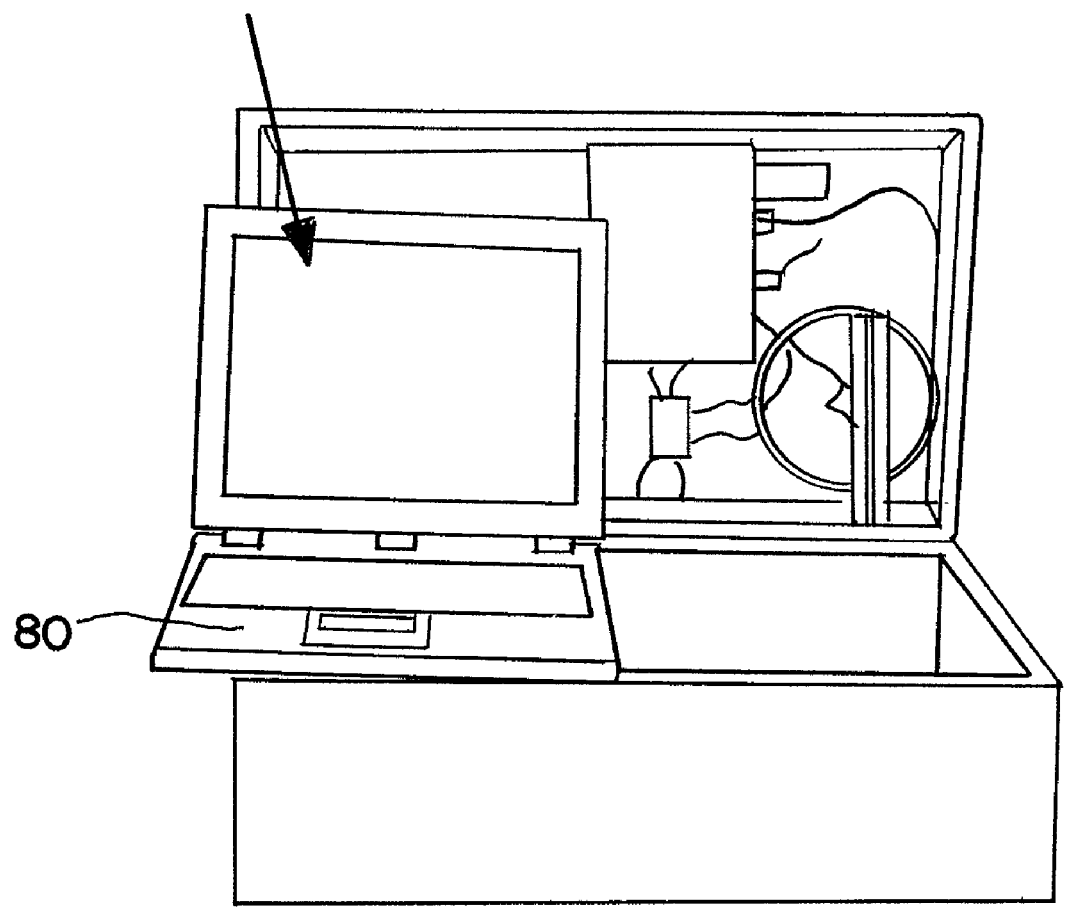
FIG. 7 is a depiction of an exemplary portable package configuration according to the invention.
Figure 8:
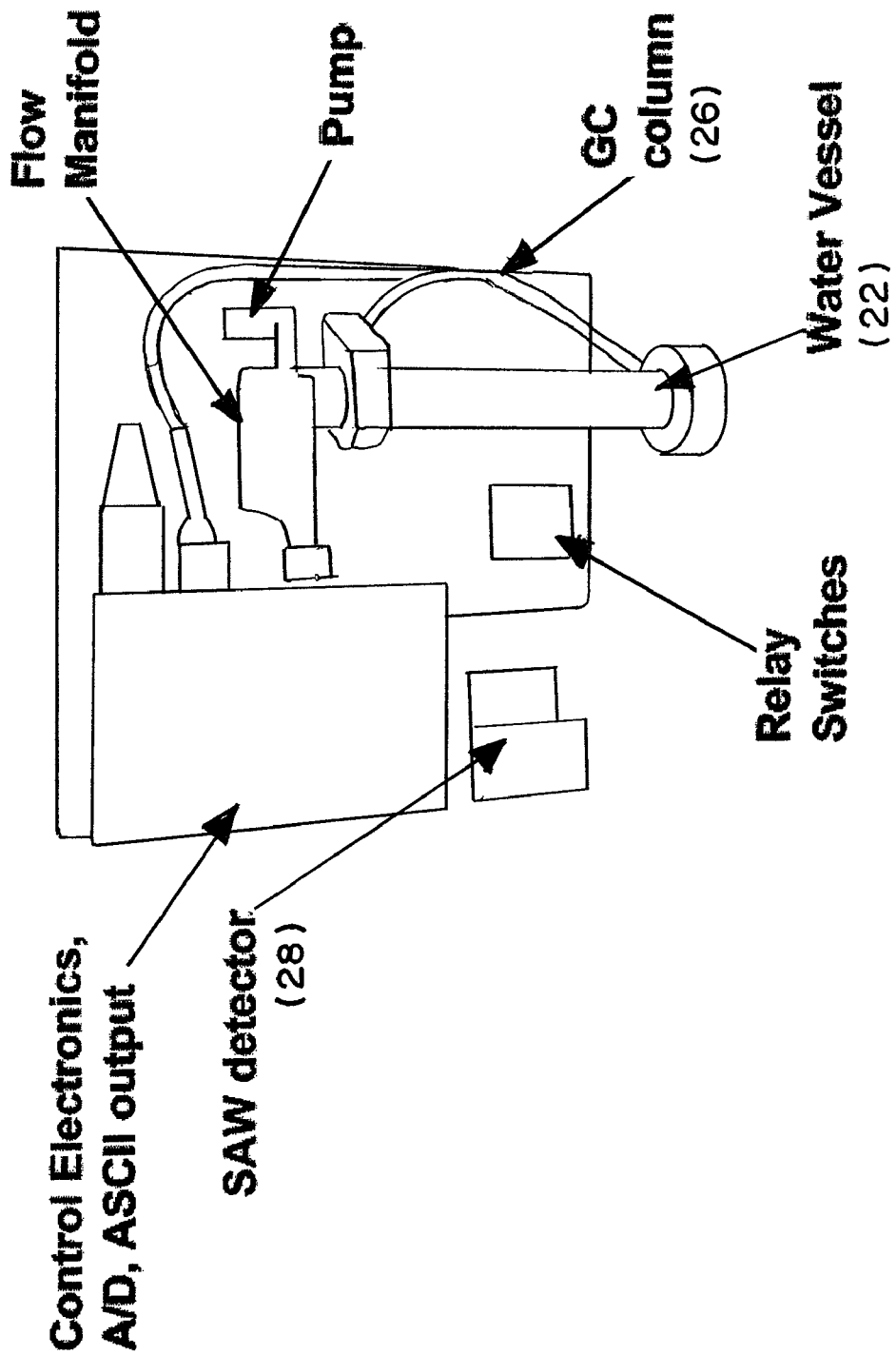
FIG. 8 is an enlargement of a portion of FIG. 7.

FIGS. 7 and 8 show a practical application of the invention in the context of a portable field system. The illustrated system can be housed when ported in a suitcase with a total weight, including batteries, preferably not exceeding 32 pounds and even having a weight under 20 pounds. Power may be supplied, for example, by one or more 12 volt rechargeable batteries with sufficient output for desired usage time. As shown, the packaged system further comprises the sample vessel 22, collector 24, separator 26, detector 28, and a data acquisition system in the form of a notebook computer 80. Also shown is a control box 30 containing control electronics, A/D devices and an ASCII output. As will be appreciated, the data acquisition system and/or display can be integrated into an onboard controller that may be provided with appropriate outputs for outputting the test results, for example to a printer or via a wired and/or wireless communication link.

In an exemplary use of the portable field system, a water sample is placed in the vessel 22. The system power is turned on (laptop data acquisition is readied), and a start button is pressed. This starts a sequence where air is drawn (as by means of a vacuum pump) through the water and through the preconcentrator, with the chemicals from the water being transferred to the preconcentrator. Valves are switched to allow the preconcentrator to have a drying flow (as needed). Flow is reversed, the preconcentrator is heated, driving the chemicals into the GC column and SAW detector. At the end of the run, when all the chemicals have eluted from the separation column, a stop button is pushed to stop the data output from the field system and stop the analysis pump.

This field system has many advantages:
1. low power—the system components can all be run on batteries,
2. size—the entire system including laptop fits in a carry-on luggage sized case.
3. the system uses air, helium or nitrogen as purge gas (if air is used, no gas tanks are required).
4. the fluidics are all robust and/or commercial components.
5. the system uses a coated SAW detector, which should provide superior detection limits compared to uncoated SAWs.
6. The system speciates (separates) the THM chemicals of interest (EPA regulated).
7. Fast. Concentration can be determined with a 10 minute purge and 2 minute analysis, whereas Hach system for THMs is >45 minutes/analysis.

As can now be appreciated, the present invention provides an improved portable detection system for volatiles in water that will have a longer life, no degradation in contact with chloroform, and requires a small volume (e.g. about 50 mL or less) of sample.

Figure 9:
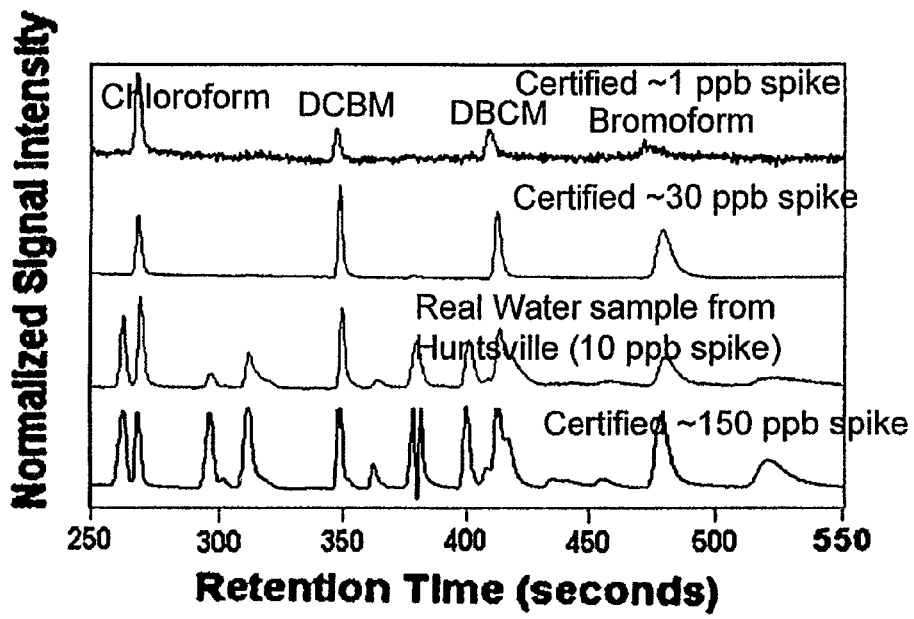
FIG. 9 is a graph showing exemplary detection of a variety of purgeable organic compounds.
Figure 10:
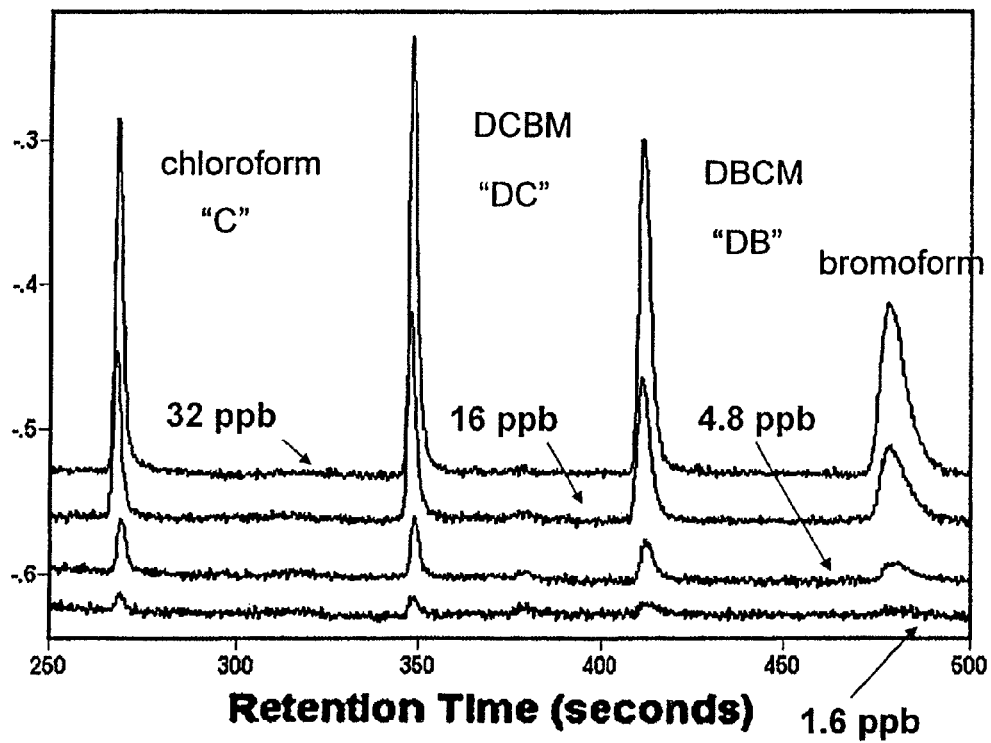
FIG. 10 is a graph showing exemplary results obtained from a sample containing four different concentrations of trihalomethanes, namely chloroform, DBCM, DCBM and bromoform.
Figure 11:
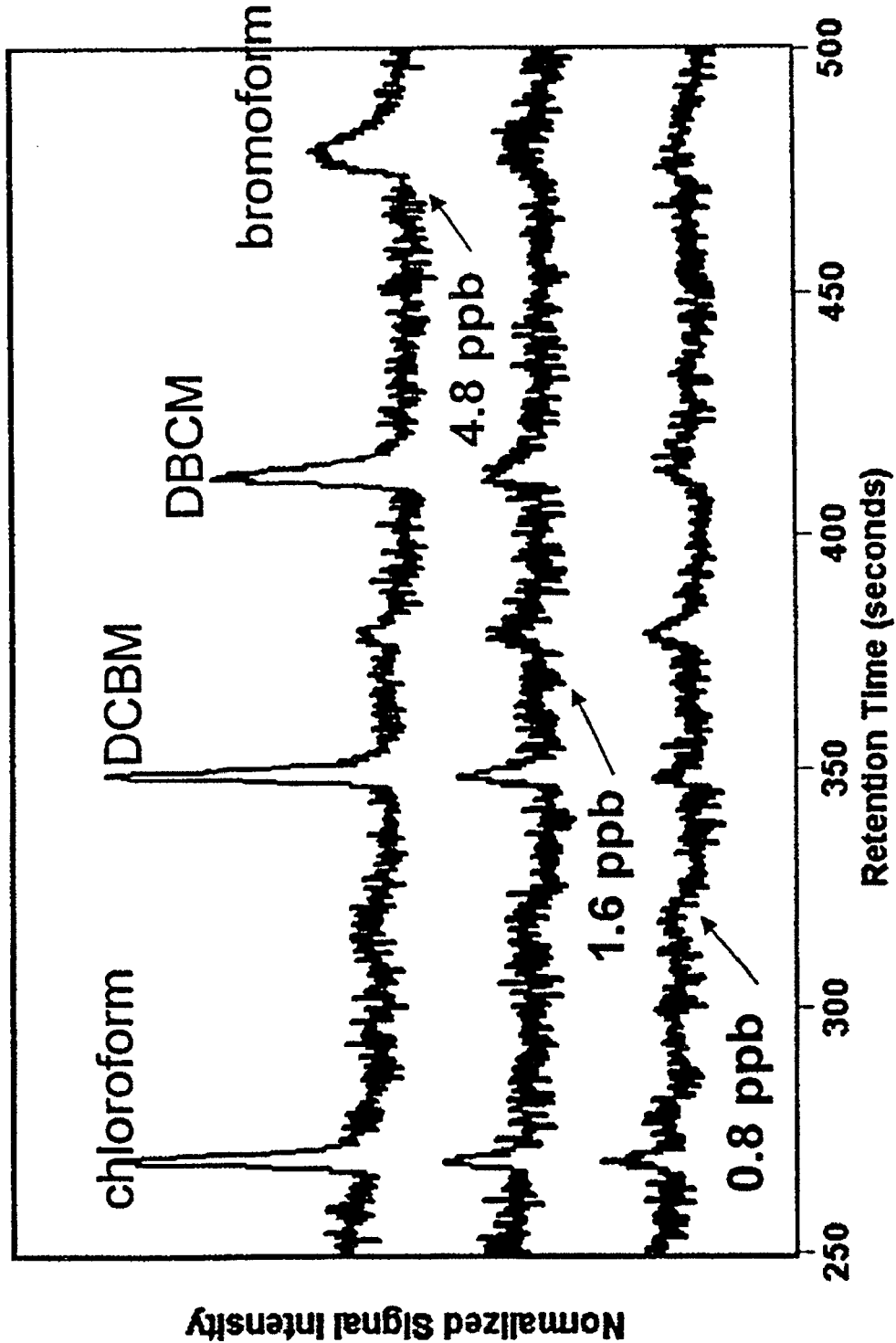
FIG. 11 is a graph showing exemplary results obtained from a water sample spiked with four component standard (all trihalomethanes of equal concentration), the data use the same y-axis with the data for different concentrations shifted for clarity.

FIG. 9 shows that the system can be used to detect a variety of purgeable organic compounds. FIG. 10 shows the results obtained from a sample containing four different concentrations of trihalomethanes, namely chloroform, dichloro-bromomethane (DCBM), dibromochloromethane (DBCM) and bromoform. FIG. 11 shows the results obtained from a water sample spiked with four component standard (all trihalomethanes of equal concentration). The data use the same y-axis with the data for different concentrations shifted for clarity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A portable field system for detecting trihalo-methane compounds in water comprising:
   a preconcentrator for collecting the trihalomethane compounds found in the water, wherein the preconcentrator includes one or more metal collection tubes containing therein a dual bed including a porous polymer resin material followed by a carbon-based adsorbent resin;
   a recirculation loop for circulating carrier gas exiting the preconcentrator back through the preconcentrator;
   a gas chromatograph column for separating the compounds as desorbed from the preconcentrator; and
   a surface acoustic wave detector for determining the mass of the compounds separated by the gas chromatograph, wherein the surface acoustic wave detector has a sensing surface with a nanoporous carbon coating.

2. A system as set forth in claim 1, wherein the surface acoustic wave detector changes its frequency depending on the mass of compound adsorbed and desorbed on the sensing surface.

3. A system as set forth in claim 1, wherein the nanoporous carbon coating was applied by pulsed laser deposition.

4. A system as set forth in claim 3, wherein the carbon coating has a carbon density of about 0.8 to about 1.3 g/cm³ and a coating thickness of about 1 to about 3 µm.

5. A system as set forth in claim 1, wherein the operating frequency of the surface acoustic wave detector is greater than 10 MHz and less than 200 MHz.

6. A system as set forth in claim 1, wherein the operating frequency of the surface acoustic wave detector is greater than 50 MHz and less than 150 MHz.

7. A system as set forth in claim 1, wherein the operating frequency of the surface acoustic wave detector is about 100 MHz.

8. A system as set forth in claim 1, further comprising a data acquisition device for receiving and processing a frequency output of the surface acoustic wave detector.

9. A system as set forth in claim 1, wherein the preconcentrator includes a porous polymer resin material as an adsorber.

10. A system as set forth in claim 1, wherein the one or more metal collection tubes have a diameter less than 0.20 inch OD, and a heating wire wrapped around the tube.

11. A system as set forth in claim 10, wherein the one or more metal collection tubes have an outer diameter of about 0.042 inch, and are coated on its inner and outer diameter surfaces with a passivating material.

12. A system as set forth in claim 1, further comprising flow control devices for directing flow through the one or more collection tubes in one direction during adsorption and in the reverse direction during desorption.

13. A system as set forth in claim 1, further comprising a sample purger for purging chemicals from a sample for adsorption in the preconcentrator.

14. A system as set forth in claim 1, wherein the one or more collection tubes are disposed between upstream and downstream manifold blocks.

15. A system as set forth in claim 1, further comprising a supply of helium for use as a carrier gas.

16. A portable field instrument for detecting purgeable trihalomethane compounds in water, comprising:
- a sample vessel wherein chemicals are purged from the water and entrained in a carrier gas;
- a preconcentrator connected to the sample purger for adsorbing the chemicals from the carrier gas, wherein the preconcentrator includes one or more metal collection tubes containing therein a dual bed including a porous polymer resin material followed by a carbon-based adsorbent resin;
- a recirculation loop for circulating carrier gas exiting the preconcentrator back through the sample vessel;
- a heater for heating the preconcentrator for desorbing the trihalomethane compounds;
- a gas chromatograph column to which the desorbed compounds are passed from the preconcentrator;
- a heater for heating the gas chromatograph column for causing the compounds to desorb after different retention times in the gas chromatograph column; and
- a surface acoustic wave detector to which the compounds are sequentially passed from the gas chromatograph column, the frequency of the surface acoustic wave detector changing as a function of the mass of compound adsorbed and desorbed from a sensing surface of the surface acoustic wave detector, whereby the mass quantity of the compounds is measured by the change of frequency of the surface acoustic wave device, wherein the surface acoustic wave detector has a sensing surface with a nanoporous carbon coating.

17. An instrument as set forth in claim 16, comprising a carrier gas supply for supplying to the sample vessel, air from the atmosphere as a carrier gas.

18. An instrument as set forth in claim 17, wherein the instrument has a sensitivity on the order of parts per billion or less.

19. A method for detecting in the field organic trihalomethane compounds in water comprising:
- bringing a portable field instrument to a testing site;
- using a preconcentrator in the instrument to collect the trihalomethane compounds from in the water, wherein the preconcentrator includes one or more metal collection tubes containing therein a dual bed including a porous polymer resin material followed by a carbon-based adsorbent resin;
- using a recirculation loop in the instrument to circulate carrier gas exiting the preconcentrator back through the preconcentrator;
- using a gas chromatograph column in the instrument to separate the compounds as desorbed from the preconcentrator; and
- using a surface acoustic wave detector in the instrument to determine the mass of the compounds separated by the gas chromatograph, wherein the surface acoustic wave detector has a sensing surface with a nanoporous carbon coating.

* * * * *